(12) United States Patent
Shiku et al.

(10) Patent No.: US 9,603,874 B2
(45) Date of Patent: *Mar. 28, 2017

(54) METHOD FOR ENHANCING A FUNCTION OF A T CELL

(71) Applicants: MIE UNIVERSITY, Mie (JP); TAKARA BIO INC., Shiga (JP)

(72) Inventors: Hiroshi Shiku, Tsu (JP); Hiroaki Ikeda, Tsu (JP); Koichi Iwamura, Tsu (JP); Junichi Mineno, Otsu (JP); Ikunoshin Kato, Otsu (JP)

(73) Assignees: Takara Bio Inc., Shiga (JP); Mie University, Mie (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/870,596

(22) Filed: Sep. 30, 2015

(65) Prior Publication Data

US 2016/0015751 A1 Jan. 21, 2016

Related U.S. Application Data

(62) Division of application No. 13/254,602, filed as application No. PCT/JP2010/053666 on Mar. 5, 2010, now Pat. No. 9,181,525.

(30) Foreign Application Priority Data

Mar. 6, 2009 (JP) .................................. 2009-053536

(51) Int. Cl.
| | |
|---|---|
| C12N 15/11 | (2006.01) |
| A61K 35/17 | (2015.01) |
| C12N 5/0783 | (2010.01) |
| C12N 15/113 | (2010.01) |
| A61K 35/12 | (2015.01) |
| A61K 39/00 | (2006.01) |

(52) U.S. Cl.
CPC ............ *A61K 35/17* (2013.01); *C12N 5/0636* (2013.01); *C12N 15/113* (2013.01); *A61K 2035/124* (2013.01); *A61K 2039/5158* (2013.01); *C12N 2310/14* (2013.01); *C12N 2501/48* (2013.01); *C12N 2501/599* (2013.01)

(58) Field of Classification Search
CPC ........................ C12N 2310/14; C12N 15/1138
See application file for complete search history.

(56) References Cited

U.S. PATENT DOCUMENTS

| 7,507,811 B2 | 3/2009 | Khvorova et al. |
| 7,595,048 B2 | 9/2009 | Honjo et al. |
| 8,507,663 B2 | 8/2013 | Defougerolles et al. |
| 9,181,525 B2 * | 11/2015 | Shiku ................... A61K 35/17 |
| 2006/0110383 A1 | 5/2006 | Honjo et al. |
| 2006/0165665 A1 | 7/2006 | Min et al. |
| 2006/0275762 A1 | 12/2006 | Saigo et al. |
| 2006/0276422 A1 * | 12/2006 | Usman ............... C12N 15/1138 514/44 A |
| 2007/0122378 A1 | 5/2007 | Freeman et al. |
| 2009/0324566 A1 | 12/2009 | Shiku et al. |
| 2010/0273213 A1 | 10/2010 | Mineno et al. |

FOREIGN PATENT DOCUMENTS

| CN | 101072880 | 11/2007 |
| EP | 1 752 536 | 2/2007 |
| JP | 2008-543774 | 12/2008 |
| WO | 2004/004771 | 1/2004 |
| WO | 2004/045543 | 6/2004 |
| WO | 2004/048566 | 6/2004 |
| WO | 2005/007855 | 1/2005 |
| WO | 2005/116204 | 12/2005 |
| WO | 2006/007539 | 1/2006 |
| WO | 2007/032255 | 3/2007 |
| WO | 2008/011344 | 1/2008 |
| WO | 2008/083174 | 7/2008 |
| WO | 2008/153029 | 12/2008 |

OTHER PUBLICATIONS

English translation of International Preliminary Report on Patentability and Written Opinion dated Oct. 18, 2011.
G. Cai et al., "PD-1 Ligands, Negative Regulators for Activation of Naïve, Memory, and Recently Activated Human CD4$^+$T Cells", Cellular Immunology, vol. 230, pp. 89-98, 2004.
J. O. Jurado et al., "Programmed Death (PD)-1:PD-Ligand 1/PD-Ligand 2 Pathway Inhibits T Cell Effector Functions During Human Tuberculosis", The Journal of Immunology, vol. 181, pp. 116-125, 2008.
L. Trautmann et al., "Upregulation of PD-1 Expression on HIV-Specific CD8$^+$T Cells Leads to Reversible Immune Dysfunction", Nature Medicine, vol. 12, No. 10, pp. 1198-1202, Oct. 2006.
M. E. Keir et al., "PD-1 and its Ligands in Tolerance and Immunity", Annu. Rev. Immunol., vol. 26, pp. 677-704, 2008.
M. E. Keir et al., "PD-1 and its Ligands in T-Cell Immunity", Current Opinion in Immunology, vol. 19, pp. 309-314, 2007.
M. J. Butte et al., "Programmed Death-1 Ligand 1 Interacts Specifically with the B7-1 Costimulatory Molecule to Inhibit T Cell Responses", Immunity, vol. 27, pp. 111-122, Jul. 2007.
G. J. Freeman et al., "Engagement of the PD-1 Immunoinhibitory Receptor by a Novel B7 Family Member Leads to Negative Regulation of Lymphocyte Activation", J. Exp. Med., vol. 192, No. 7, pp. 1027-1034, Oct. 2, 2000.

(Continued)

*Primary Examiner* — Brian Whiteman
(74) *Attorney, Agent, or Firm* — Wenderoth, Lind & Ponack, L.L.P.

(57) ABSTRACT

Disclosed is a method for enhancing the function of a T cell, which is characterized by inhibiting the expression of programmed death-1 ligand 1 (PD-L1) and/or programmed death-1 ligand 2 (PD-L2) in the T cell. Also disclosed is a function-enhanced T cell which is produced by the function enhancement method. Further disclosed is a therapeutic agent comprising the function-enhanced T cell. The T cell can enhance an immune response to cancer, and is useful in an immunotherapy effective for cancer and the treatment or prevention of infectious diseases and autoimmune diseases.

11 Claims, 5 Drawing Sheets

(56) References Cited

OTHER PUBLICATIONS

Y. Latchman et al., "PD-L2 is a Second Ligand for PD-1 and Inhibits T Cell Activation", Nature Immunology, vol. 2, No. 3, pp. 261-267, Mar. 2001.
Y. Miyahara et al., "Determination of Cellularly Processed HLA-A2402-Restricted Novel CTL Epitopes Derived from Two Cancer Germ Line Genes, MAGE-A4 and SAGE", Clinical Cancer Res., vol. 11, No. 15, pp. 5581-5589, Aug. 1, 2005.
S. Kawai et al., "New Procedure for DNA Transfection with Polycation and Dimethyl Sulfoxide", Molecular and Cellular Biology, vol. 4, No. 6, pp. 1172-1174, Jun. 1984.
Chinese Office Action and Search Report, with English translation, issued Oct. 8, 2012 in corresponding Chinese Patent Application No. 201080020173.X.
Extended European Search Report issued May 28, 2013 in corresponding European Application No. 10748842.1.
SEO et al., "Co-inhibitory role of T-cell-associated B7-H1 and B7-Dc in the T-cell immune response", Immunology Letters, vol. 102, 2006, pp. 222-228, XP02499070.
Chinese Office Action, with English translation, issued Jun. 26, 2013 in corresponding Chinese Patent Application No. 201080020173.X.
Chinese Office Action, with partial English translation, issued Dec. 27, 2013 in corresponding Chinese Patent Application No. 201080020173.
Full English translation of Chinese Office Action issued Dec. 27, 2013 in corresponding Chinese Patent Application No. 201080020173.
Chinese Decision on Rejection dated Jul. 21, 2014 issued in corresponding Chinese Patent Application No. 201080020173.X (with English translation).
Japanese Office Action dated Aug. 5, 2014 issued in corresponding Japanese Application No. 2011-502824 (with English translations).
European Office Action dated Sep. 25, 2014 issued in corresponding European Patent Application No. 10748842.1.
Japanese Office Action issued Jul. 19, 2016, in corresponding Japanese Patent Application No. 2011-502824 (with English translation).
Summons to attend oral proceedings pursuant to Rule 115(1) EPC issued Jun. 9, 2016, in corresponding European Patent Application No. 10748842.1.
Chinese Notice of Reexamination dated Apr. 28, 2016, issued in corresponding Chinese Patent Application No. 201080020173.X (with English translation).
English Abstract of Reexamination Decision dated Oct. 17, 2016 issued in corresponding Chinese Patent Application No. 201080020173.X.

* cited by examiner

SEQUENCE LISTING

```
<160> NUMBER OF SEQ ID NOS: 19

<210> SEQ ID NO 1
<211> LENGTH: 25
<212> TYPE: RNA
<213> ORGANISM: Artificial
<220> FEATURE:
<223> OTHER INFORMATION: siRNA specific for PD-L1

<400> SEQUENCE: 1
aaugcguuca gcaaaugcca guagg                                           25

<210> SEQ ID NO 2
<211> LENGTH: 25
<212> TYPE: RNA
<213> ORGANISM: Artificial
<220> FEATURE:
<223> OTHER INFORMATION: siRNA specific for PD-L2

<400> SEQUENCE: 2
aaaugaaagc aaugaugcag gaggg                                           25

<210> SEQ ID NO 3
<211> LENGTH: 25
<212> TYPE: RNA
<213> ORGANISM: Artificial
<220> FEATURE:
<223> OTHER INFORMATION: siRNA specific for PD-1

<400> SEQUENCE: 3
uuacgucucc uccaaaugug uauca                                           25

<210> SEQ ID NO 4
```

```
<211> LENGTH: 657
<212> TYPE: DNA
<213> ORGANISM: Artificial
<220> FEATURE:
<223> OTHER INFORMATION: siRNA cluster PDL1-PDL2-TCR alpha-TCR beta

<400> SEQUENCE: 4
atcgggccca gatcttattt caaatttagc aggaaaaaag agaacatcac cttgtaaaac      60
tgaagattgt gaccagtcag aataatgtcg actacaagcg aattactcat gctacagtca     120
agatgagtaa ttcgcttgta gtcgcattat ggtgacagct gcctcgggaa gccaagttgg     180
gctttaaagt gcagggcctg ctgatgttga gtgcttttttg ttcggacagt accaatgcat    240
aaactgtgct ctgagaagct tatgcattgg tactgtccca taagaagtta tgtattcatc     300
caataattca agccaagcaa gtatataggt gttttaatag ttttttgtttg cagtcctctg    360
ttgtaaggat tctgatgtgt acacagggaa gcgagtctgt acacatcaga atccttactg     420
gtggcctgct atttccttca aatgaatgat ttttactaat tttgtgtact tttattgtgt     480
cgatgtagaa tctgcctggt ctatctgatg tgacagcttc tgtagcaccc accatccctct    540
atgagattag tgctcctggt tgatctcata gaggatggtg gtactgctag ctgtagaact     600
ccagcttcgg cctgtcgccc aatcaaactg tcctgttact ggcggccgca tcgattc       657

<210> SEQ ID NO 5
<211> LENGTH: 351
<212> TYPE: DNA
<213> ORGANISM: Artificial
<220> FEATURE:
<223> OTHER INFORMATION: siRNA cluster PDL1-PDL2

<400> SEQUENCE: 5
atcgggccca gatcttattt caaatttagc aggaaaaaag agaacatcac cttgtaaaac      60
tgaagattgt gaccagtcag aataatgtcg actacaagcg aattactcat gctacagtca     120
agatgagtaa ttcgcttgta gtcgcattat ggtgacagct gcctcgggaa gccaagttgg     180
gctttaaagt gcagggcctg ctgatgttga gtgcttttttg ttcggacagt accaatgcat    240
aaactgtgct ctgagaagct tatgcattgg tactgtccca taagaagtta tgtattcatc     300
caataattca agccaagcaa gtatataggt gttttaatag cggccgctcc c              351

<210> SEQ ID NO 6
<211> LENGTH: 200
<212> TYPE: DNA
<213> ORGANISM: Artificial
<220> FEATURE:
<223> OTHER INFORMATION: siRNA cluster PDL1

<400> SEQUENCE: 6
atcgggccca gatcttattt caaatttagc aggaaaaaag agaacatcac cttgtaaaac      60
tgaagattgt gaccagtcag aataatgtcg actacaagcg aattactcat gctacagtca     120
agatgagtaa ttcgcttgta gtcgcattat ggtgacagct gcctcgggaa gccaagttgg     180
gctttaaagc ggccgcatat                                                 200

<210> SEQ ID NO 7
<211> LENGTH: 203
<212> TYPE: DNA
<213> ORGANISM: Artificial
```

```
<220> FEATURE:
<223> OTHER INFORMATION: siRNA cluster PDL2

<400> SEQUENCE: 7
atcgggccca gatcttattt caaatttagc aggaaaaaag agaacatcac cttgtaaaac      60
tgaagattgt gaccagtcag aataatgtgg acagtaccaa tgcataaact gtgctctgag     120
aagcttatgc attggtactg tcccattatg gtgacagctg cctcgggaag ccaagttggg     180
ctttaaagcg gccgcatcga ttc                                             203

<210> SEQ ID NO 8
<211> LENGTH: 19
<212> TYPE: RNA
<213> ORGANISM: Artificial
<220> FEATURE:
<223> OTHER INFORMATION: siRNA for PD-L1 (sh831)

<400> SEQUENCE: 8
cuaauugucu auugggaaa                                                   19

<210> SEQ ID NO 9
<211> LENGTH: 19
<212> TYPE: RNA
<213> ORGANISM: Artificial
<220> FEATURE:
<223> OTHER INFORMATION: siRNA for PD-L1 (sh832)

<400> SEQUENCE: 9
cgacuacaag cgaauuacu                                                   19

<210> SEQ ID NO 10
<211> LENGTH: 19
<212> TYPE: RNA
<213> ORGANISM: Artificial
<220> FEATURE:
<223> OTHER INFORMATION: siRNA for PD-L2 (sh833)

<400> SEQUENCE: 10
ggacgaagga caguaccaa                                                   19

<210> SEQ ID NO 11
<211> LENGTH: 19
<212> TYPE: RNA
<213> ORGANISM: Artificial
<220> FEATURE:
<223> OTHER INFORMATION: siRNA for PD-L2 (sh834)

<400> SEQUENCE: 11
ggacaguacc aaugcauaa                                                   19

<210> SEQ ID NO 12
<211> LENGTH: 20
<212> TYPE: DNA
<213> ORGANISM: Artificial
<220> FEATURE:
<223> OTHER INFORMATION: real time PCR F-primer for PD-L1

<400> SEQUENCE: 12
tatggtggtg ccgactacaa                                                  20

<210> SEQ ID NO 13
<211> LENGTH: 20
<212> TYPE: DNA
<213> ORGANISM: Artificial
<220> FEATURE:
```

```
<223> OTHER INFORMATION: real time PCR R-primer for PD-L1

<400> SEQUENCE: 13
tgcttgtcca gatgacttcg                                            20

<210> SEQ ID NO 14
<211> LENGTH: 20
<212> TYPE: DNA
<213> ORGANISM: Artificial
<220> FEATURE:
<223> OTHER INFORMATION: real time PCR F-primer for PD-L2

<400> SEQUENCE: 14
gggacgaagg acactaccaa                                            20

<210> SEQ ID NO 15
<211> LENGTH: 20
<212> TYPE: DNA
<213> ORGANISM: Artificial
<220> FEATURE:
<223> OTHER INFORMATION: real time PCR R-primer for PD-L2

<400> SEQUENCE: 15
tttggccagg atacttctgc                                            20

<210> SEQ ID NO 16
<211> LENGTH: 20
<212> TYPE: DNA
<213> ORGANISM: Artificial
<220> FEATURE:
<223> OTHER INFORMATION: real time PCR F-primer for GAPDH

<400> SEQUENCE: 16
gagtcaacgg atttggtcgt                                            20

<210> SEQ ID NO 17
<211> LENGTH: 20
<212> TYPE: DNA
<213> ORGANISM: Artificial
<220> FEATURE:
<223> OTHER INFORMATION: real time PCR R-primer for GAPDH

<400> SEQUENCE: 17
gatctcgctc ctggaagatg                                            20

<210> SEQ ID NO 18
<211> LENGTH: 19
<212> TYPE: RNA
<213> ORGANISM: Artificial
<220> FEATURE:
<223> OTHER INFORMATION: siRNA for TCR alpha

<400> SEQUENCE: 18
guaaggauuc ugaugugua                                             19

<210> SEQ ID NO 19
<211> LENGTH: 19
<212> TYPE: RNA
<213> ORGANISM: Artificial
<220> FEATURE:
<223> OTHER INFORMATION: siRNA for TCR beta

<400> SEQUENCE: 19
ccaccauccu cuaugagau                                             19
```

METHOD FOR ENHANCING A FUNCTION OF A T CELL

TECHNICAL FIELD

The present invention relates to a method for enhancing the function of a T cell by suppressing the expression of Programmed Death-1 Ligand 1 (PD-L1) and/or Programmed Death-1 Ligand 2 (PD-L2) of the T cell, etc.

BACKGROUND OF THE INVENTION

A signal via the B7: CD28 costimulatory molecular family is deeply involved in activation, inhibition and adjustment of a T cell reaction. It has been known that a PD-1 (Programmed Death-1) molecule belonging to the B7: CD28 costimulatory molecular family reacts with PD-L1 and PD-L2, and negatively controls the T cell reaction (Non-Patent Document 1). At first, it has been suggested that PD-1 expressed on a T cell reacts with PD-L1 expressed on an antigen presenting cell or a cancer cell, or PD-L2 on an antigen presenting cell to inhibit the activation of the T cell.

On the other hand, it has been known that PD-L1 is also expressed on a T cell. Recently, a possibility that PD-L1 binds with not only PD-1 but also B7-1 (CD80), and PD-L1 present on a T cell sends a negative signal to the T cell has been demonstrated (Non-Patent Document 2). However, what physiological and pathological roles are played by PD-L1 expressed on a T cell, in an immune reaction, is entirely unknown. Regarding PD-L2, it has been only known so far that it is expressed on a dendritic cell, a macrophage, a B1B cell, and a mast cell derived from bone marrow only upon induction, and its expression on a T cell is not clear. Therefore, a role played by PD-L2, which is physiologically or forcibly expressed on a T cell, is not entirely known.

There has been demonstrated a possibility that an immune response inhibiting signal from a costimulatory molecule, a representative of which is CTLA4 or PD-1, induces tolerance (immunological tolerance) via suppression of priming or the effector function at the initial stage of an autoreactive T cell while balancing with an immune response activating signal from a costimulatory molecule, a representative of which is a T cell receptor (TCR) or CD28, thereby protecting tissues from the autoreactive T cell and, on the other hand, controlling infection immunity or tumor immunity. In addition, it has been thought that certain tumors or viruses suppress the activation and proliferation of a T cell by a direct or indirect mechanism utilizing the costimulatory molecule, to weaken an immune reaction against themselves. Further, it has been thought that in a part of diseases attributed to a functional disorder of a T cell, abnormality of the costimulatory molecule is a cause for a functional disorder of a T cell.

PRIOR ART DOCUMENTS

Non-Patent Document

Non-Patent Document 1: Keir M, and other three persons, Annu. Rev. Immunol., Vol. 26, pp. 677-704 (2008)

Non-Patent Document 2: Butte M, and other four persons, Immunity, Vol. 27, pp. 111-122 (2007)

SUMMARY OF THE INVENTION

Problems to be Solved by the Invention

An object of the present invention is to provide a method for enhancing the function of a T cell, and a T cell with enhanced function.

Means for Solving the Problems

The present inventors have found that it is possible to control a T cell immune response by artificially controlling the expression of PD-L1 and/or PD-L2 of a T cell. Particularly, the present inventors have found that reduction of the expression of PD-L1 and/or PD-L2 in an anti-tumor T cell enhances the anti-tumor effect of the T cell, and thus it results in completion of the present invention.

That is, the present invention relates to:

[1] a method for enhancing the function of a T cell, comprising suppressing the expression of Programmed Death-1 Ligand 1 (PD-L1) and/or Programmed Death-1 Ligand 2 (PD-L2) of the T cell;

[2] the method for enhancing the function of a T cell according to [1], wherein the T cell is a cytotoxic T cell or a regulatory T cell;

[3] the method for enhancing the function of a T cell according to [2], wherein the regulatory T cell is a helper T cell, a controlling T cell or a Th17 cell;

[4] the method for enhancing the function of a T cell according to [1], wherein the function enhancement is the production enhancement of T cell interferon-γ (IFN-γ);

[5] the method for enhancing the function of a T cell according to [1], wherein the expression of PD-L1 and/or PD-L2 is suppressed by siRNA for PD-L1 and/or PD-L2;

[6] a T cell with enhanced function, which is suppressed in the expression of PD-L1 and/or PD-L2;

[7] the T cell with enhanced function according to [6], wherein the T cell is a cytotoxic T cell or a regulatory T cell;

[8] the T cell with enhanced function according to [7], wherein the regulatory T cell is a helper T cell, a controlling T cell or a Th17 cell;

[9] the T cell with enhanced function according to [6], wherein the function enhancement is the production enhancement of T cell interferon-γ (IFN-γ);

[10] the T cell with enhanced function according to [6], wherein the expression of PD-L1 and/or PD-L2 is suppressed by siRNA for PD-L1 and/or PD-L2; and

[11] a therapeutic agent for a disease showing sensitivity to the T cell with enhanced function according to any one of [6] to [10], comprising the T cell as an active ingredient.

Advantages of the Invention

According to the present invention, a method for enhancing the function of a T cell, a T cell with enhanced function, etc., are provided. This T cell enhances an immune response to cancer, and is useful in effective cancer immunotherapy, or treatment or prevention of an infection disease or an autoimmune disease.

DETAILED DESCRIPTION OF THE PREFERRED EMBODIMENTS

Herein, "enhanced function of a T cell" means that the effector function of the T cell is improved. The enhanced function of the T cell, which does not limit the present invention, includes an improvement in the proliferation rate of the T cell, an increase in the production amount of cytokine, or an improvement in cytotoxicity. Further, the enhanced function of the T cell includes cancellation and suppression of tolerance of the T cell in the suppressed state such as the anergy (unresponsive) state, or the rest state, that is, transfer of the T cell from the suppressed state into the state where the T cell responds to stimulation from the outside.

In the present invention, "anergy" includes unresponsiveness to an immune cell to stimulation, for example, stimulation by an activation receptor or cytokine. The anergy may occur due to, for example, exposure to an immune suppressor or exposure to an antigen in a high dose. Such anergy is generally antigen-specific, and continues even after completion of exposure to a tolerized antigen. For example, the anergy in a T cell is characterized by failure of production of cytokine, for example, interleukin (IL)-2. The T cell anergy occurs when a first signal (signal via TCR or CD-3) is received in the absence of a second signal (costimulatory signal) upon exposure of a T cell to an antigen.

Herein, "PD-L1" means ligand 1 of PD-1, which is a costimulatory molecule expressed on a so-called antigen presenting cell such as an activated monocyte or a dendritic cell, and is also referred to as B7-H1. The nucleotide sequence of human PD-L1 is shown by GenBank Acc. No. AF233516, and the nucleotide sequence of mouse PD-L1 is shown by NM_021893 (Freeman et al. (2000) J. Exp. Med. 192:1027).

Herein, "PD-L2" means ligand 2 of PD-1, and is also referred to as B7-DC. The nucleotide sequence of human PD-L2 is shown by GenBank Acc. No. NM_025239, and the nucleotide sequence of mouse PD-L2 is shown by NM_021896 (Nature Immunology, 2001, Vol. 2, No. 3, pp. 261-267).

Herein, "T cell" is also referred to as T lymphocyte, and means a cell derived from thymus among lymphocytes involved in an immune response. The T cell includes any of a CD8-positive T cell (cytotoxic T cell: CTL), a CD4-positive T cell (helper T cell), a suppressor T cell, a regulatory T cell such as a controlling T cell, an effector cell, a naive T cell, a memory T cell, an αβT cell expressing TCR α and β chains, and a γδT cell expressing TCR γ and δ chains. The T cell includes a precursor cell of a T cell in which differentiation into a T cell is directed. Examples of "cell populations containing T cells" include, in addition to body fluids such as blood (peripheral blood, umbilical blood etc.) and bone marrow fluids, cell populations containing peripheral blood mononuclear cells (PBMC), hematopoietic cells, hematopoietic stem cells, umbilical blood mononuclear cells etc., which have been collected, isolated, purified or induced from the body fluids. Further, a variety of cell populations containing T cells and derived from hematopoietic cells can be used in the present invention. These cells may have been activated by cytokine such as IL-2 in vivo or ex vivo. As these cells, any of cells collected from a living body, or cells obtained via ex vivo culture, for example, a T cell population obtained by the method of the present invention as it is, or obtained by freeze preservation, can be used.

Herein, "cancer" means a malignant tumor, and refers to a cell exhibiting abnormal proliferation phenotype or the abnormal cell state, which has a feature of exhibiting autonomous proliferation and, as a result, uncontrollable cell proliferation. "Tumor cells" include "malignant tumor cells" or "benign tumor cells", and are also referred to as "cells derived from neoplasm".

Herein, "expression" means generation of mRNA by transcription from nucleic acids such as genes, polynucleotides, and oligonucleotides, or generation of a protein or a polypeptide by transcription from mRNA. "Suppression of expression" refers to a decrease of a transcription product or a translation product in a significant amount as compared with the case of no suppression. The suppression of expression herein shows, for example, a decrease of a transcription product or a translation product in an amount of 30% or more, preferably 50% or more, more preferably 70% or more, and further preferably 90% or more.

(1) Method for Enhancing Function of T Cell and T Cell with Enhanced Function of the Present Invention The method for enhancing the function of a T cell of the present invention is a method including the step of suppressing the expression of PD-L1 and/or PD-L2 of the T cell. In addition, the T cell with enhanced function of the present invention is a cell obtained by the method for enhancing the function of a T cell of the present invention. The method of enhancing the function of a T cell of the present invention makes it possible to improve the effector function of the T cell, including an improvement in the proliferation rate of the T cell, an increase in the production amount of cytokine or an improvement in cytotoxicity. Further, the suppressed state of the T cell such as the anergy state, or the rest state is cancelled or suppressed, and the sensitivity of the T cell to stimulation from the outside is improved. The thus obtained T cell with enhanced function of the present invention is useful in treating or preventing cancer, an infection disease or an autoimmune disease.

In the method of the present invention, the step of suppressing the expression of PD-L1 and/or PD-L2 of the T cell can be performed ex vivo or in vivo.

The method of the present invention in which the step is performed ex vivo includes the steps of: (a) preparing a T cell or a cell population containing a T cell, and (b) suppressing the expression of PD-L1 and/or PD-L2 of the T cell obtained in the step (a) to prepare a T cell with enhanced function. The method can be applied to cell immunotherapy including adoptive immunotherapy, and is useful. The step (a) may be the step of separating a T cell or a cell population containing a T cell from a living body, or the step of preparing an established T cell or a cell population containing a T cell. Further, the method of the present invention may includes the step of separating the cell population containing a T cell from cell populations to prepare a cell sub-population and/or the step of culturing and stimulating the cell population. These steps can be performed at an arbitrary stage before, after or simultaneous with the step (a) and the step (b). In the method of the present invention in which the step of suppressing the expression of PD-L1 and/or PD-L2 of the T cell is performed ex vivo, the amount and kind of the cell to which the method is applied can be controlled through a suitable means, for example, preparation of a cell sub-population, or culturing or stimulation of the cell population. Therefore, a harmful event such as autoimmunity, which is concerned when a substance suppressing the expression of PD-L1 and/or PD-L2 or a substance inhibiting signal transmission is administered to a living body, can be reduced, and therefore it is extremely useful.

The step of separating the cell population and cell sub-population containing a T cell can be performed, for example, by fractionation of a mononuclear cell fraction by density gradient centrifugation, or a separation means using the surface marker of the T cell as an index. Examples of the surface marker include CD3, CD8 and CD4, and separation methods depending on these surface markers are known in the art. For example, the step can be performed by mixing a carrier such as beads or a culturing container on which an anti-CD8 antibody has been immobilized, with a cell population containing a T cell, and recovering a CD8-positive T cell bound to the carrier. As the beads on which an anti-CD8 antibody has been immobilized, for example, CD8 Micro-Beads (manufactured by Miltenyi Biotec), Dynabeads M450 CD8 (manufactured by Invitrogen), and Eligix anti-CD8 mAb coated nickel particles (manufactured by Biotransplant) can be suitably used. This is also the same as in implementation using CD4 as an index and, for example, CD4 MicroBeads (manufactured by Miltenyi Biotec), Dynabeads M-450 CD4 (manufactured by Invitrogen) can be suitably used.

The step of culturing the cell population and cell sub-population containing a T cell can be performed by selecting suitable known culturing conditions depending on the cell population. In addition, in the step of stimulating the cell population, known proteins and chemical ingredients, etc., may be added to the medium to perform culturing. For example, cytokines, chemokines or other ingredients may be added to the medium. Herein, the cytokine is not particularly limited as far as it can act on the T cell, and examples thereof include IL-2, IFN-γ, transforming growth factor (TGF)-β, IL-15, IL-7, IFN-α, IL-12, CD40L, and IL-27. From the viewpoint of enhancing cellular immunity, particularly suitably, IL-2, IFN-γ, or IL-12 is used and, from the viewpoint of improvement in survival of a transferred T cell in vivo, IL-7, IL-15 or IL-21 is suitably used. In addition, the chemokine is not particularly limited as far as it acts on the T cell and exhibits migration activity, and examples thereof include RANTES, CCL21, MIP1α, MIP1β, CCL19, CXCL12, IP-10 and MIG. The stimulation of the cell population can be performed by the presence of a ligand for a molecule present on the surface of the T cell, for example, CD3, CD28, or CD44 and/or an antibody to the molecule. Further, the cell population can be stimulated by contacting with other lymphocytes such as antigen presenting cells (dendritic cell) presenting a target peptide such as a peptide derived from a cancer antigen on the surface of a cell.

When the step of suppressing the expression of PD-L1 and/or PD-L2 of the T cell is performed in vivo, the step is performed by administering a means to specifically suppress the expression thereof described later to a living body. Thereupon, a suitable drug delivery system (e.g. liposome, fine particles, microcapsule etc.) can be utilized. Further, for example, utilizing the delivery system using the surface marker of the T cell as an index, the expression of PD-L1 and/or PD-L2 of the T cell can be specifically suppressed.

Examples of the means to suppress the expression of PD-L1 and/or PD-L2 of the T cell include utilization of nucleic acids such as siRNA for PD-L1 and/or PD-L2, an antisense nucleotide, and a ribozyme.

The utilization of siRNA in the present invention is for the purpose of selectively suppressing the expression of PD-L1 and/or PD-L2, and is based on RNA interference (RNAi) utilizing a double-stranded RNA molecule having a sequence homologous with the nucleotide sequence of mRNA which is transcribed from a gene encoding PD-L1 and/or PD-L2, and a sequence complementary with the nucleotide sequence. Herein, "having a sequence homologous with the nucleotide sequence of mRNA which is transcribed from a gene encoding PD-L1 and/or PD-L2, and a sequence complementary with the nucleotide sequence" not only refers to the fact that each sequence is completely homologous or complementary with the nucleotide sequence of mRNA, but also includes the fact that each sequence is substantially homologous or complementary in such a range that the desired function is exerted. The double-stranded RNA molecule is referred to as siRNA (short interfering RNA). The siRNA may be one kind of siRNA which is homologous/complementary with one region of mRNA which is transcribed from a gene encoding PD-L1 and/or PD-L2, or may be siRNA including a plurality of RNA molecules which are homologous/complementary with different regions.

Examples of the chain length of the siRNA used in the present invention include, from the viewpoint of suppression of interferon response in a mammal cell, those in which one strand of a duplex constituting the siRNA has a chain length of 13 to 29 base pairs, preferably a chain length of 15 to 25 base pairs, further preferably a chain length of 20 to 25 base pairs. In addition, all of the nucleotide sequences of the chain lengths may be derived from the nucleotide sequence of the mRNA of PD-L1 and/or PD-L2, or a part thereof may be derived from the nucleotide sequence. Further, the siRNA used in the present invention, from the viewpoint of effectiveness of RNA interference in a mammal cell, may be, for example, a shape of double-stranded RNA having a single-stranded region which is protruded on a 3'-terminal side by 2 to 4 nucleotides, further preferably a shape of double-stranded RNA having a single-stranded region which is protruded on a 3'-terminal side by 2 nucleotides. As the protruded single-stranded region, deoxythymidine residue of continuous 2 to 4 nucleotides (TT, TTT or TTTT) is exemplified.

The siRNA used in the present invention is mainly comprised of ribonucleotides, and a part thereof may include nucleotides other than ribonucleotides, for example, deoxyribonucleotides, a derivative of deoxyribonucleotides, a derivative of ribonucleotides, etc. The siRNA can be synthesized by a known chemical synthesis method, but the method is not particularly limited. It may be enzymatically (e.g., using an RNA polymerase) prepared using a suitable template nucleic acid. The siRNA used in the present invention may be in the form of single-stranded RNA which can form a duplex in the molecule, and single-stranded RNA with a stem-loop structure (short hairpin structure: sh structure) having the siRNA part as a stem and an arbitrary sequence as a loop (shRNA) is exemplified. As the arbitrary sequence, a sequence of 1 to 30 nucleotides is exemplified, and a sequence of preferably 1 to 25 nucleotides, further preferably 5 to 22 nucleotides is used.

The sequence of the siRNA can be appropriately designed based on a gene sequence whose expression is desired to be suppressed. Many siRNA design algorisms have been reported (see, e.g., WO 2004/0455543, and WO 2004/048566), and a commercially available software can also be used. In addition, there are many companies which design siRNA from information of a gene sequence whose expression is desired to be suppressed, and synthesize and provide the siRNA. Therefore, a person skilled in the art can easily obtain the siRNA based on the gene sequence whose expression is desired to be suppressed. As the siRNA used in the present invention, any can be used as far as it is siRNA which selectively suppresses the expression of PD-L1 and/or PD-L2. For example, siRNA including the nucleotide sequence of SEQ ID NO: 1 or SEQ ID NO: 9 can be used for PD-L1, and siRNA including the nucleotide sequence of SEQ ID NO: 2 or SEQ ID NO: 11 can be used for PD-L2, without particular limitation.

In the present invention, an antisense nucleotide can be used for suppressing the expression of PD-L1 and/or PD-L2. The antisense nucleotide is used for suppressing the expression of a protein, for example, by directly interfering translation of the mRNA molecule of PD-L1 and/or PD-L2, by degradation of mRNA by an RNA degradation enzyme H, by interfering the 5' capping of mRNA, by masking the 5' cap, by preventing binding of a translation factor with mRNA, or by inhibiting polyadenylation of mRNA. The suppression of the expression of a protein occurs by hybridization between an antisense nucleotide and the mRNA of PD-L1 and/or PD-L2. In order to reduce stability of, or degrade mRNA, as a target of the antisense nucleotide, a specific targeting site on the mRNA is selected. When one or more target sites are identified, a nucleotide having a nucleotide sequence sufficiently complementary with the target site (that is, which hybridizes sufficiently and with sufficient specificity under the physiological conditions) is designed.

As the antisense nucleotide used in the method of the present invention, for example, a nucleotide having a chain length of 8 to 100 nucleotides, preferably 10 to 80 nucleotides, more preferably 14 to 35 nucleotides is exemplified.

In the present invention, nucleic acids such as siRNA and an antisense nucleotide used in suppressing the expression of PD-L1 and/or PD-L2 may be directly introduced into a cell, or a nucleic acid construct which has been designed so that the siRNA or the antisense nucleotide is transcribed in a cell may be introduced into a cell. When directly introduced into a cell, a reagent for introducing a nucleic acid such as TransIT-TKO (manufactured by Mirus), and Human T Cell Nucleofector Kit (Amaxa) can be suitably used. On the other hand, when the nucleic acid construct in which the RNA molecule is transcribed is used, a nucleic acid construct can be used which is functionally connected downstream of a promoter capable of exerting the function in the T cell in the state where transcription of a nucleic acid encoding the siRNA or the antisense nucleotide can occur, but it does not particularly limit the present invention. In addition, in order to attain effective transcription of a gene, other regulatory sequences cooperating with a promoter or a transcription initiation site, for example, an enhancer sequence or a terminator sequence may be present in the nucleic acid construct. In addition, for the purpose of insertion of a subject to be introduced into a chromosome of the T cell by homologous recombination, for example, the gene may be arranged between flanking sequences including nucleotide sequences, each having homology with nucleotide sequences on both sides of a desired target insertion site of a gene in the chromosome.

The promoter used in the nucleic acid construct is not particularly limited as far as it can function in a mammal cell, and examples thereof include an RNA polymerase II promoter, an RNA polymerase III promoter, and an artificially regulatable promoter. Example of the RNA polymerase II promoter includes a CMV promoter. In addition, examples of the RNA polymerase III-based promoter include a tRNA promoter, a U6snRNA promoter, and a histone H1 promoter. As the promoter which can be artificially regulated with tetracycline, a promoter which can be regulated with tetracycline is exemplified, and examples thereof include a tetracycline-regulated U6 promoter, and a TR promoter. In addition, combination of the promoter with the Cre-loxP system makes it possible to control transcription more strictly.

The nucleic acid construct used for transcribing siRNA can be constructed so that a sense strand and an antisense strand of double-stranded RNA which can suppress the function of an objective gene are transcribed by the following system: (A) a tandem type in which a nucleic acid encoding sense RNA and a nucleic acid encoding antisense RNA are connected downstream of different two promoters, respectively, and these two transcription units are arranged in the forward direction, and the sense RNA and the antisense RNA are transcribed separately, (B) a type in which a nucleic acid encoding sense RNA and a nucleic acid encoding antisense RNA are arranged downstream of one promoter, respectively, in the forward direction, and RNA having a stem-loop type (or short hairpin type) in which the sense RNA and the antisense RNA are connected directly or with a loop is transcribed, or (C) a counter type in which a promoter is arranged on both end sides of nucleic acids encoding a sense strand and an antisense strand (with both strands, respectively), respectively, and both RNA strands are transcribed with separate promoters. In the present invention, the tandem type, the stem-loop type or the counter type can be used depending on the use conditions, for example, the kind of a cell, the kind of a sense sequence or an antisense sequence etc.

The nucleic acid construct used in the present invention may be incorporated into a suitable vector, for example, a plasmid vector or a virus vector so as to more stably exert the effect in a cell. Further, the nucleic acid construct of the present invention may be incorporated on the chromosome DNA of a cell. Examples of the plasmid vector include, but are not particularly limited to, a piGENE tRNA plasmid (trade name, manufactured by iGENE), siLentGene (manufactured by Promega), and pSEC Hygro Vector (manufactured by Ambion). In order to introduce the plasmid vector into a cell, a method using a carrier such as a liposome or ligand-polylysine, a calcium phosphate method, an electroporation method, a particle gun method, etc., can be used.

The virus vector is not particularly limited, and usually, a known virus vector used in a gene introduction method, for example, a retrovirus vector (including lentivirus vector, pseudo type vector), an adenovirus vector, an adeno-associated virus vector, a simian virus vector, a vaccinia virus vector or a sendai virus vector is used. Particularly preferably, a retrovirus vector, an adenovirus vector or a lentivirus vector is used. As the virus vector, a virus vector in which the replicating ability is defective so that it cannot self-replicate in an infected cell is preferable. In addition, upon gene introduction, a substance improving a gene introduction efficiency such as retronectin (registered trademark, manufactured by TAKARA BIO INC.) can be also used. An example of a commercially available adenovirus vector includes Knockout Adenoviral RNAi System (manufactured by Clonetech) and, examples of a commercially available retrovirus vector include a pSINsi vector (manufactured by TAKARA BIO INC.) and pSIREN-RetroQ Vector (manufactured by Clonetech), respectively. In the case of the virus vector, it can be introduced into an objective cell utilizing the ability of the virus to infect a cell.

In the method of the present invention, a means to suppress the expression of PD-L1 and/or PD-L2 is implemented on the T cell. That is, in the step (b), for example, a helper T cell, a suppressor T cell, a controlling T cell, a cytotoxic T cell (CTL), a naïve T cell, a memory T cell, an αβT cell expressing TCR α and β chains or a γδT cell expressing TCR γ and δ chains, or a cell population containing these cells, blood (peripheral blood, umbilical blood etc.) or a bone marrow fluid can be used. These T cells may be derived from a mammal, or may be derived from either human or a non-human mammal.

The suppression of the expression of PD-L1 and/or PD-L2 can be confirmed by quantitative determination of the PD-L1 and/or PD-L2 protein, or quantitative determination of RNA transcribed from the PD-L1 and/or PD-L2 gene.

The function enhancement of the T cell in the method of the present invention can be assessed at a plurality of time points before and after each step using a cytokine assay, an antigen-specific cell assay (tetramer assay), a proliferation assay, a cytolytic cell assay, or an in vivo delayed hypersensitivity test using a recombinant tumor-associated antigen or an immunogenic fragment or an antigen-derived peptide. Examples of an additional method for measuring an increase in an immune response include a delayed hypersensitivity test, flow cytometry using a peptide major histocompatibility gene complex tetramer. a lymphocyte proliferation assay, an enzyme-linked immunosorbent assay, an enzyme-linked immunospot assay, cytokine flow cytometry, a direct cytotoxity assay, measurement of cytokine mRNA by a quantitative reverse transcriptase polymerase chain reaction, or an assay which is currently used for measuring a T cell response such as a limiting dilution method.

The T cell with enhanced function of the present invention is enhanced in the function of the T cell as compared with a control T cell in which the expression of PD-L1 and/or PD-L2 is not suppressed. The T cell with enhanced function of the present invention is increased in, for example, the production amount of IFN-γ as compared with a control T cell. The T cell of the present invention is increased in the production amount of IFN-γ by 10% or more, preferably 20% or more, more preferably 30% or more as compared with a control T cell.

Examples of one aspect of the present invention include a method of further enhancing the function of the T cell, in addition to the suppression of the expression of PD-L1 and/or PD-L2. For example, introduction of a gene encoding TCR recognizing a desired antigen into a T cell makes it possible to obtain a T cell to which specificity for the antigen is imparted, and whose effector function is improved. Examples of the antigen include, but are not particularly limited to, a tumor antigen, a microorganism and a virus-derived antigen. Regarding TCR to a variety of antigens, its amino acid sequence, and the nucleotide sequence of a gene encoding the amino acid sequence are known and, construction of a vector for TCR expression based on the information and introduction of the vector into a T cell makes it possible to produce a T cell exerting an antigen-specific action. Thereupon, simultaneous introduction of a nucleic acid construct for suppressing the expression of PD-L1 and/or PD-L2 into a T cell, or incorporation of the construct into the vector for TCR expression makes it possible to improve the effector function of an antigen-specific T cell.

When TCR including α and β chains is artificially expressed in a T cell, mispairing between the α and β chains derived from an endogenous TCR gene possessed by the T cell itself, etc., may hinder the imparting of desired antigen specificity. For example, implementation of codon conversion of an introduced TCR gene or knockdown of an endogenous TCT gene utilizing siRNA, which is disclosed in WO 2008/153029, makes it possible to produce a T cell which has acquired high antigenic specificity. The method for enhancing the function of a T cell of the present invention can also be utilized in producing such a T cell.

(2) Treating Method or Preventing Method Using T Cell with Enhanced Function of the Present Invention The treating method or preventing method of the present invention has a feature of administering the T cell prepared by the method for enhancing the function of the present invention in (1) to a living body. That is, the treating method or preventing method of the present invention includes the step of: (c) administering the T cell with enhanced function obtained in the step (b) to a living body. The disease for which the T cell with enhanced function of the present invention is administered is not particularly limited as far as it is a disease exhibiting sensitivity to the T cell, and examples thereof include cancer (leukemia, solid tumor, etc.), hepatitis, influenza, an infectious disease, a cause of which is a virus such as HIV, a bacterium or a fungus, for example, tuberculosis, MRSA, VRE, deep mycosis. In addition, the cell of the present invention can also be utilized in bone mallow transplantation, or prevention of an infectious disease after radiation, or donor lymphocyte infusion for the purpose of remission of recurrent leukemia. Further, the cell improves the function of a controlling T cell, and can be utilized in preventing or treating an autoimmune disease.

In the method of the present invention, the T cell with enhanced function can be administered to a subject intradermally, intramuscularly, subcutaneously, intraperitoneally, intraarterially, intravenously (including a method performed by an indwelling catheter), intratumorally, or into an afferent lymph vessel.

In the treating method or preventing method of the present invention, the T cell with enhanced function to be administered may be a cell which is self to a living body, or may be a cross-derived cell.

An immune response induced in implementation of the present invention can be assessed in a living body before first administration of the T cell with enhanced function of the present invention, or at various time points after initiation of treatment, using an antigen-specific cell assay, a proliferation assay, a cytolytic cell assay, or an in vivo delayed hypersensitivity test using a recombinant tumor-associated antigen or an immunogenic fragment or an antigen-derived peptide. Examples of an additional method for measuring an increase in an immune response include a delayed hypersensitivity test, flow cytometry using a peptide major histocompatibility gene complex tetramer. a lymphocyte proliferation assay, an enzyme-linked immunosorbent assay, an enzyme-linked immunospot assay, cytokine flow cytometry, a direct cytotoxity assay, measurement of cytokine mRNA by a quantitative reverse transcriptase polymerase chain reaction, or an assay which is currently used for measuring a T cell response such as a limiting dilution method. Further, an immune response can be assessed by a weight, diameter or malignant degree of a tumor possessed by a living body, the infection virus amount or infection bacterium amount of a subject, or the survival rate or survival term of a subject.

In the method of the present invention, examples of the amount of the T cell with enhanced function to be administered to a living body include, but are not particularly limited to, preferably $1 \times 10^6$ to $1 \times 10^{12}$ cells/day, more preferably $1 \times 10^7$ to $5 \times 10^{11}$ cells/day, and further preferably $1 \times 10^8$ to $2 \times 10^{11}$ cells/day per adult a day.

(3) Therapeutic Agent for Disease Containing T Cell with Enhanced Function of the Present Invention The T cell with enhanced function prepared by the method for enhancing the function of the present invention in (1), and a composition containing the T cell as an active ingredient are useful as a therapeutic agent for a disease having sensitivity to the T cell, for example, the aforementioned cancer, hepatitis or an infectious disease.

The therapeutic agent of the present invention can be prepared, for example, by mixing the T cell prepared by the method of present invention as an active ingredient with, for example, known organic or inorganic carrier, excipient, stabilizer, etc., which are suitable for parenteral administration, according to a method known in the pharmacy filed. In addition, use thereof may be performed according to the treating method of the present invention in (2).

EXAMPLES

The present invention will be described further concretely below by way of Examples, but the present invention is not limited to only the scope of the following Examples.

Example 1

Confirmation of Expression of PD-L1 in CD8-Positive T Cell

Figure 1:
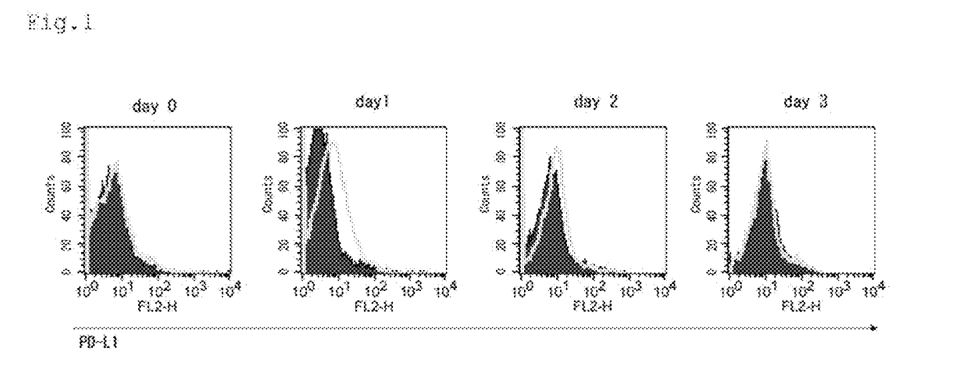
FIG. 1 is a view analyzing the expression of PD-L1 of a CD8-positive T cell.

According to WO 2007/032255, HLA-A24 restrictive MAGE-A $4_{143-151}$-specific cytotoxic CD8-positive T cell clone 2-28 (Miyahara Y, and other 13 persons, Clin. Cancer Res., Vol. 11, pp. 5581-5589 (2005), hereinafter, referred to as CD8-positive T cell clone 2-28) and a MAGE-A$4_{143-151}$ peptide were prepared. The CD8-positive T cell clone 2-28 was co-cultured at 37° C. with self lymphoblastoid cell line (LCL) which had been irradiated with 80 Gly X-ray and had been pulsed with MAGE-A$4_{143-151}$ peptide, PD-L1 on the cell surface after 0 day, 1 day, 2 days and 3 days was stained with an anti-human PD-L1 antibody (manufactured by BD bioscience), and analyzed with a flow cytometer. FIG. 1 shows the results of analysis with a flow cytometer. The expression of PD-L1 was highest after 1 day of culturing.

Example 2

Suppression of Expression of PD-L1 and PD-L2 of CD8-Positive T Cell by RNA Interference SiRNA specific for PD-L1 having a sequence described in SEQ ID NO: 1, siRNA specific for PD-L2 having a sequence described in SEQ ID NO: 2, or negative control siRNA (all manufactured by Invitrogen) was introduced into CD8-positive T cell clone 2-28 by electroporation.

A cell with siRNA for PD-L1 introduced therein was cultured for 3 days, and then co-cultured at 37° C. with self LCL which had been irradiated with 80 Gly X-ray and had been pulsed with a MAGE-A$4_{143-151}$ pep tide. On the next day, this was stained with an anti-human PD-L1 antibody, and the expression of PD-L1 on the cell surface was analyzed with a flow cytometer.

Regarding a cell with siRNA for PD-L2 introduced therein, the cell was stained with an anti-human PD-L2 antibody (manufactured by BD bioscience) and the expression of PD-L2 in the cell was analyzed with a flow cytometer, after 2 days and 3 days after introduction.

Figure 2:
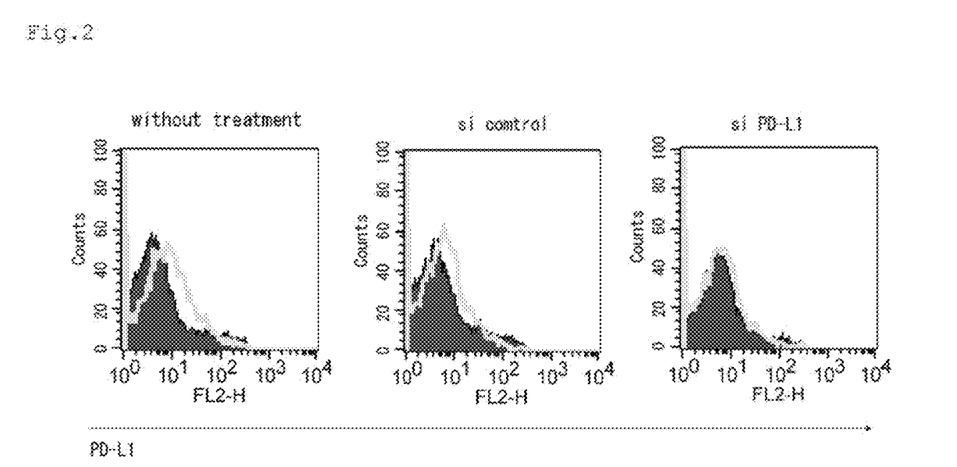
FIG. 2 is a view analyzing the expression of PD-L1 of a CD8-positive T cell.
Figure 3:
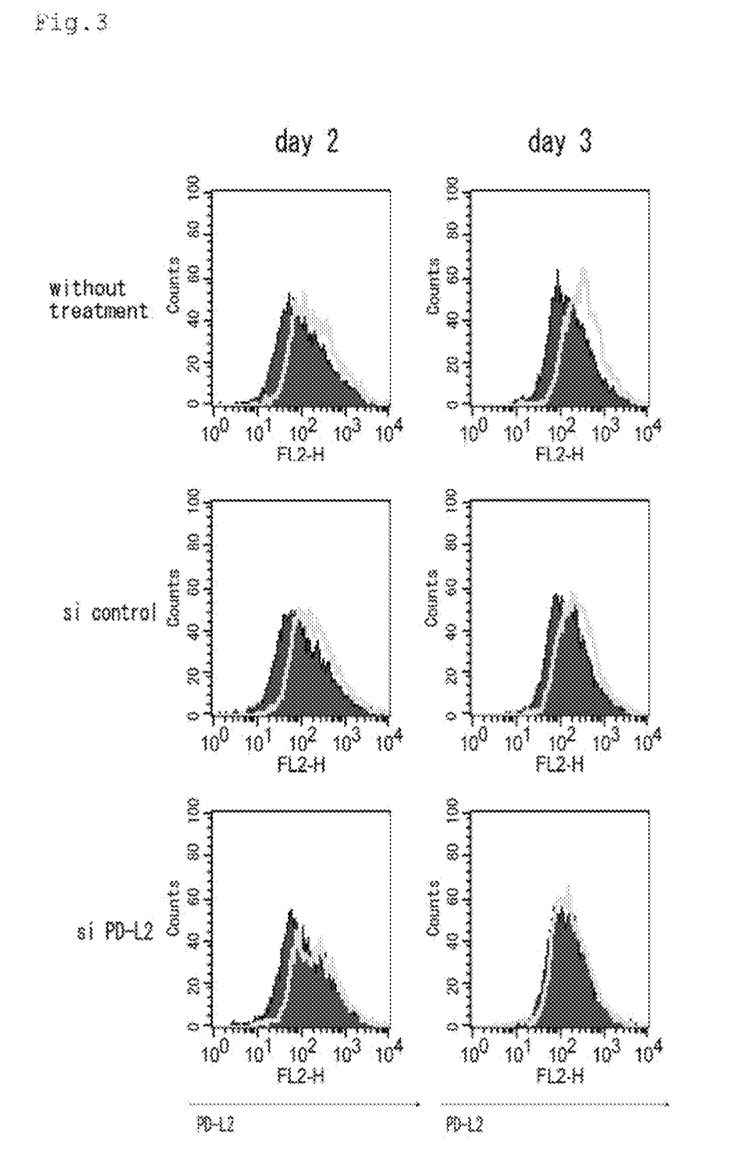
FIG. 3 is a view analyzing the expression of PD-L2 of a CD8-positive T cell.

The results of analysis of PD-L1 are shown in FIG. 2, and the results of analysis of PD-L2 are shown in FIG. 3, respectively. In the cell with no siRNA introduced therein (non-treatment) and the cell with negative control siRNA introduced therein (si control), suppression of the expression of PD-L1 or PD-L2 was not seen. In the cell with siRNA specific for PD-L1 introduced therein (si PD-L1), and the cell with siRNA specific for PD-L2 introduced therein (si PD-L2), suppression of the expression of PD-L1 and PD-L2 was seen, respectively.

Example 3

Promotion of Production of IFN-γ of PD-L1 and PD-L2-Expressing CD8-Positive T-Cell by RNA Interference Negative control siRNA, siRNA specific for PD-1 having a sequence described in SEQ ID NO: 3 (manufactured by Invitrogen), siRNA specific for PD-L1 having a sequence described in SEQ ID NO: 1, or siRNA specific for PD-L2 having a sequence described in SEQ ID NO: 2 was introduced into CD8-positive T cell clone 2-28 by electroporation. After culturing for 3 days, this cell was mixed with a cell in which self LCL had been pulsed with a MAGE-A$4_{143-151}$ peptide at a ratio of 4:1 or 2:1, and the mixture was co-cultured at 37° C. and, on the next day, the concentration of IFN-γ in each culturing supernatant was measured by an ELISA method.

Figure 4:
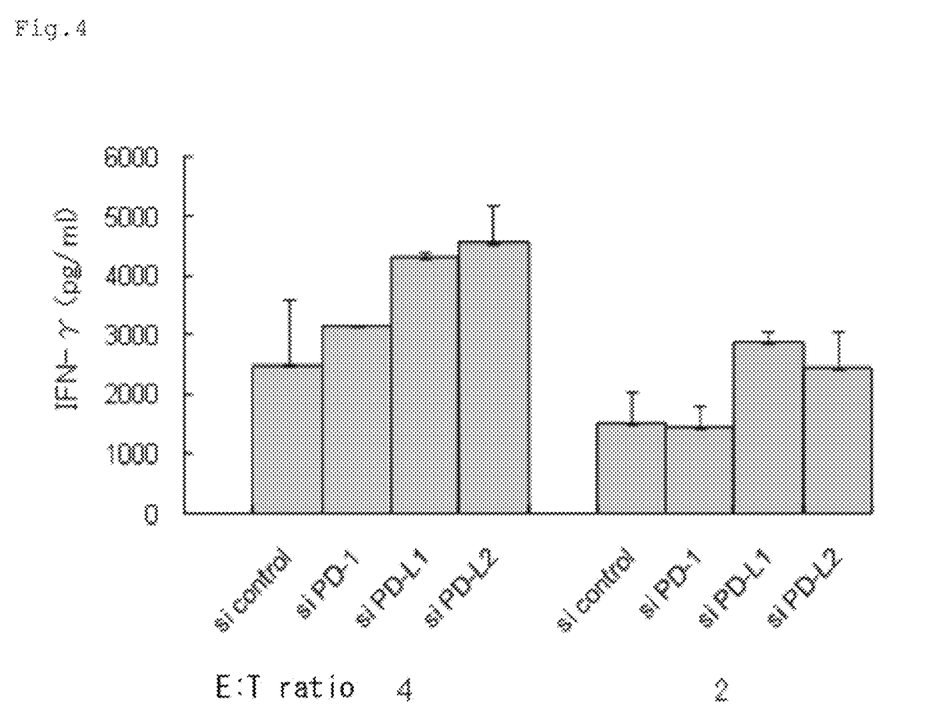
FIG. 4 is a view showing the concentration of interferon γ (IFN-γ) of a CD8-positive T cell.

The concentration of IFN-γ in each cell supernatant is shown in FIG. 4. In the cell with siRNA specific for PD-1 introduced therein (si PD-1), change in the concentration of IFN-γ was not seen at culturing with both mixing ratios, as compared with the cell with negative control siRNA introduced therein. In the cell with siRNA specific for PD-L1 introduced therein and the cell with siRNA specific for PD-L2 introduced therein, an increase in the concentration of IFN-γ was significantly seen, respectively, as compared with the cell with negative control siRNA introduced therein and the cell with siRNA specific for PD-1 introduced therein.

Example 4

Promotion of Expression of IFN-γ of PD-L1 and PD-L2-Expressing CD4-Positive T Cell by RNA Interference Negative control siRNA, siRNA specific for PD-1 having a sequence described in SEQ ID NO: 3, siRNA specific for PD-L1 having a sequence described in SEQ ID NO: 1, or siRNA specific for PD-L1 having a sequence described in SEQ ID NO: 2 was introduced into MAGE-A$4_{46-66}$-specific CD4-positive T cell clone 5 by electroporation, and this was cultured for 3 days. This cell was mixed with a cell in which self LCL had been pulsed with a MAGE-A$4_{46-66}$ peptide at 2:1, and the mixture was cultured at 37° C. and, on the next day, the concentration of IFN-γ in each culturing supernatant was measured by an ELISA method.

Figure 5:
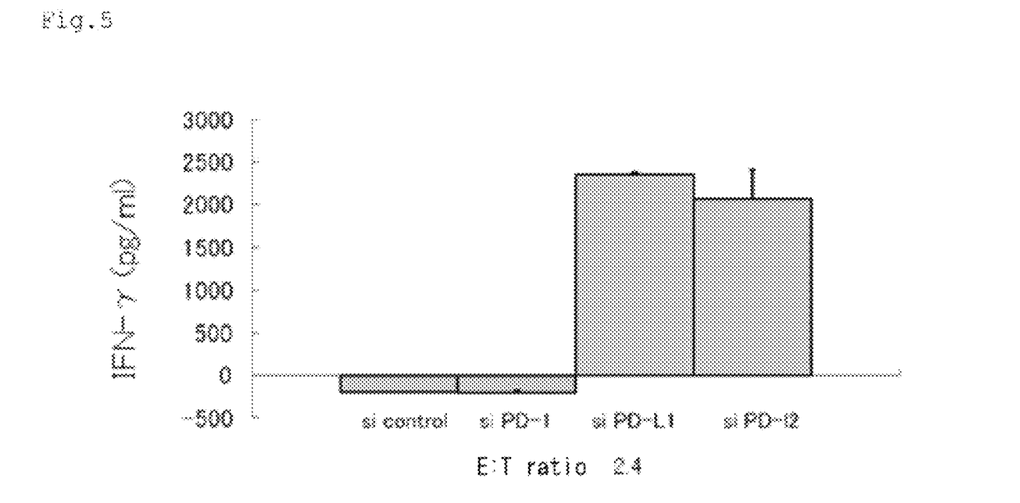
FIG. 5 is a view showing the concentration of IFN-γ of a CD4-positive T cell.

The concentration of IFN-γ in each cell supernatant is shown in FIG. 5. In the cell with negative control siRNA introduced therein, and the cell with siRNA specific for PD-1 introduced therein, the expression of IFN-γ was not seen. In the cell with siRNA specific for PD-L1 introduced therein and the cell with siRNA specific for PD-L2 introduced therein, the expression of IFN-γ was significantly seen.

Example 5

Selection of siRNA for Suppressing Expression of PD-L1 and PD-L2

SiRNAs specific for PD-L1 each having a sequence described in SEQ ID NO: 8 or 9 (sh831, sh832), or siRNAs specific for PD-L2 each having a sequence described in SEQ ID NO: 10 or 11 (sh833, sh834) (all manufactured by TAKARA BIO INC.), or the negative control siRNA used in Example 2 was introduced into LCL by electroporation, this was cultured at 37° C. for 2 days, total RNA was extracted from each cell, the expression of PD-L1 and PD-L2 was measured by real time RT-PCR using QuanTitect SYBR PCR Kit (manufactured by QIAGEN), and siRNA having strong expression suppressing power was selected.

Sequences of primers for real time RT-PCR used in measuring the expression of PD-L1 are shown in SEQ ID Nos.: 12 and 13, sequences of primers for real time RT-PCR used in measuring the expression of PD-L2 are shown in SEQ ID Nos.: 14 and 15, and sequences of primers for real time RT-PCR of human GAPDH (glyceraldehyde-3-phosphate dehydrogenase) as a subject of measurement of the expression are shown in SEQ ID Nos.: 16 and 17, respectively.

Figure 6:
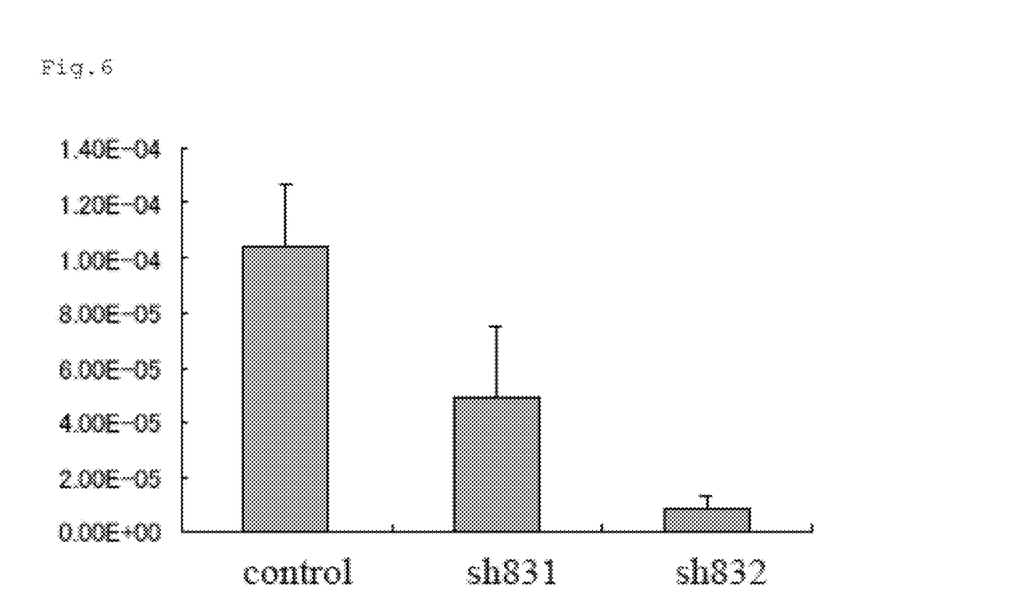
FIG. 6 is a view analyzing the expression of PD-L1 of LCL.
Figure 7:
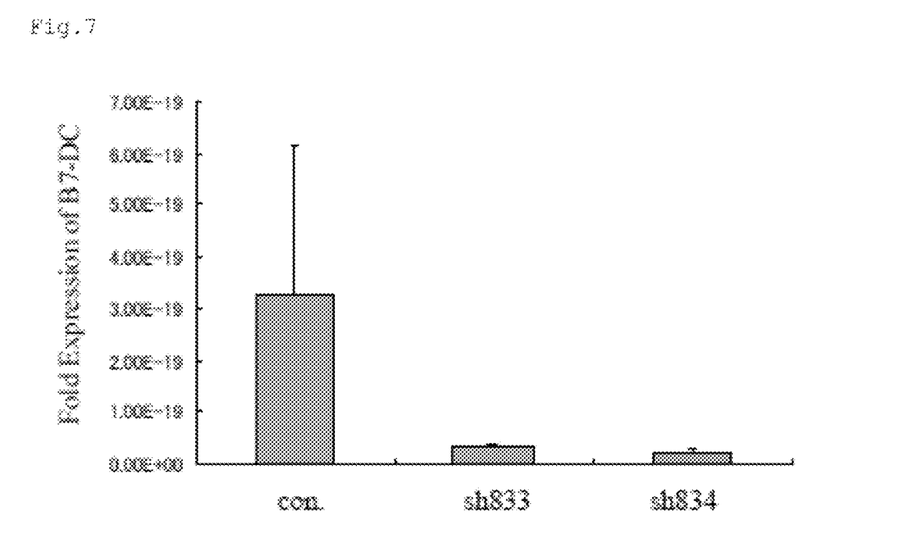
FIG. 7 is a view analyzing the expression of PD-L2 of LCL.

The results of real time RT-PCR of PD-L1 are shown in FIG. 6, and the results of real time RT-PCR of PD-L2 are shown in FIG. 7. In the figures, an ordinate axis shows the ratio of the expression of PD-L1 or PD-L2 relative to the expression of human GAPDH. From this result, sh832 shown in SEQ ID NO: 9 as siRNA specific for PD-L1, and sh834 shown in SEQ ID NO: 11 as siRNA specific for PD-L2 were selected.

Example 6

Production of Codon Conversion-Type TCR-Expressing Retrovirus Vector

According to WO 2008/153029, pMS-Ma2 and pMS-Pb2 were produced. These vectors include the retrovirus vector system based on MSCV (Murine Stem Cell Virus). Further, those vectors include genes encoding TCR α and β chains recognizing tumor antigen MAGE-A4, respectively and, in these genes, codons were converted so that the expression is not suppressed by RNA interference with siRNA on TCR described later (hereinafter, a gene in which codons are converted is referred to as codon conversion-type).

Example 7

Production of Codon Conversion-Type TCR and siRNA-Expressing Retrovirus Vector

A codon conversion-type TCRα gene was excised with MluI and BglII from pMS-Ma2 produced in Example 6, and TCRα-MluI/BglII was prepared. A siRNA cluster, a PDL1-PDL2-TCRα-TCRβ artificially synthesized gene shown in SEQ ID NO: 4 was digested with BglII and NotI, and cloned into the MluI-NotI site of pMS-Pb2 together with TCRα-MluI/BglII, to prepare an MS-aPb1-siPDL_1/2_siTCR vector (vector 1). The vector 1 expresses the codon conversion-type TCR, and can express siRNAs for PD-L1, PD-L2, TCRα and TCRβ shown in SEQ ID Nos.: 9, 11, 18 and 19. Among them, siRNA s for TCRα and TCRβ suppress the expression of endogeneous wild-type TCR, and does not suppress the expression of the codon conversion-type TCR.

Further, a siRNA cluster, a PDL1-PDL2 artificially synthesized gene shown in SEQ ID NO: 5, a siRNA cluster PDL1 artificially synthesized gene shown in SEQ ID NO: 6, and a siRNA cluster PDL2 artificially synthesized gene shown in SEQ ID NO: 7 were prepared, and an MS-aPb1-siPDL_1/2_vector (vector 2), an MS-aPb1-siPDL_1 vector (vector 3), and an MS-aPb1-siPDL_2 vector (vector 4) were prepared as in the vector 1. The summary of genes expressed by respective vectors is shown in Table 1.

TABLE 1

| Expressed gene | Vector 1 | Vector 2 | Vector 3 | Vector 4 |
|---|---|---|---|---|
| Codon conversion-type TCRα gene | ○ | ○ | ○ | ○ |
| Codon conversion-type TCRβ gene | ○ | ○ | ○ | ○ |
| siRNA for TCRα | ○ | | | |
| siRNA for TCRβ | ○ | | | |
| siRNA for PD-L1 | ○ | ○ | ○ | |
| siRNA for PD-L2 | ○ | ○ | | ○ |

Example 8

Production of Codon Conversion-Type TCR and siRNA-Expressing Retrovirus Solution

*Escherichia coli* JM109 was transformed with the vectors 1 to 4 prepared in Example 7, and plasmid DNA was purified using QIAGEN Plasmid Midi Kit (manufactured by QIAGEN) to provide DNA for transfection.

Each prepared DNA for transfection was transfected into a 293T cell according to a product protocol using Retrovirus Packing Kit Eco (manufactured by TAKARA BIO INC.) to obtain each ecotropic virus supernatant solution. This supernatant solution was filtered with a 0.45 µm filter (Milex HV, manufactured by Millipore), and made to infect a PG13 cell (ATCC CRL-10686) by a method using polybrene [Kawai et al., Mol. Cell. Biol., Vol. 4, p. 1172, (1984)], the resulting culture supernatant of the cell was recovered, and filtered with a 0.45 µm filter to prepare a retrovirus solution.

Example 9

Infection of Human Peripheral Blood Mononuclear Cell with Codon Conversion-Type TCR and siRNA-Co-Expressing Retrovirus Vector A peripheral blood mononuclear cell (PBMC) separated from human peripheral blood was infected with the retrovirus solution produced in Example 8 two times according to a manual using Retronectin (registered trademark, manufactured by TAKARA BIO INC.) to produce codon conversion-type TCR and a siRNA-co-expressing introduction peripheral blood mononuclear cell. After 3 days from second virus infection, the cell was recovered, genome was extracted with FastPure DNA Kit (TAKARA BIO INC.), and the average provirus copy number in each cell genome was calculated with Proviral Copy Number Detection Primer Set (manufactured by TAKARA BIO INC.) and CycleavePCR Core Kit (manufactured by TAKARA BIO INC.). The provirus copy number of PBMC infected with the virus solution containing the vectors 1 to 4 was 4.6 copies/cell, 2.2 copies/cell, 3.2 copies/cell, and 4.5 copies/cell, respectively. Then, after 5 days from second virus infection, the cell was recovered, and stained with HLA-A2402 MAGE-A4 tetramer PE (manufactured by MBL) and Human CD8-FITC CONJUGATE (manufactured by Becton, Dickinson), and the ratio of a cell which is CD8-positive and tetramer-positive according to a flow cytometer was determined.

Figure 8:
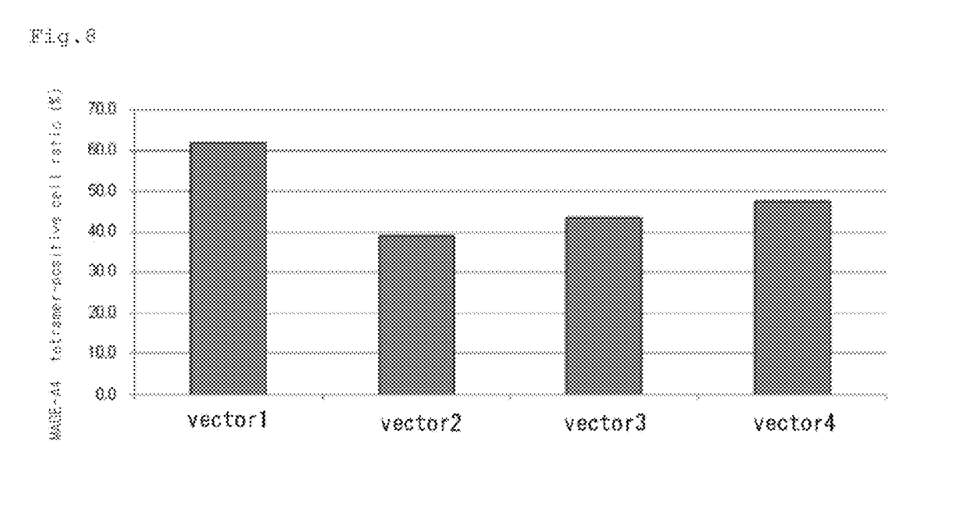
FIG. 8 is a view showing the ratio of a CD8-positive tetramer-positive T cell.

The rate of an MAGE-A4 tetramer-positive cell is shown in FIG. 8. An abscissa axis indicates an introduced retrovirus vector, and an ordinate axis indicates the rate of an MAGE-A4 tetramer-positive cell (%). As shown in FIG. 8, the expression of an anti-MAGE-A4TCRα/β composite protein by gene introduction into a human peripheral blood mononuclear cell was confirmed by each retrovirus vector introduction. In addition, the expression of siRNA for PD-L1 and PD-L2 expressed by the retrovirus vector did not greatly influence on the expression of the introduced codon conversion-type TCR. Further, siRNAs for TCRα and TCRβ enhanced the rate of codon conversion-type TCRα/β composite protein expression by the effect of suppressing the expression of a wild-type endogenous TCR gene by siRNA.

INDUSTRIAL APPLICABILITY

The present invention provides a method for enhancing the function of a T cell, and a T cell with enhanced function. This T cell enhances an immune response to cancer, and can be utilized in effective cancer immunotherapy, and treatment or prevention of an infection disease or an autoimmune disease.

Sequence Listing Free Text

SEQ ID NO:1: siRNA specific for PD-L1
SEQ ID NO:2: siRNA specific for PD-L2
SEQ ID NO:3: siRNA specific for PD-1
SEQ ID NO:4: siRNA cluster PDL1-PDL2-TCR alpha-TCR beta
SEQ ID NO:5: siRNA cluster PDL1-PDL2
SEQ ID NO:6: siRNA cluster PDL1
SEQ ID NO:7: siRNA cluster PDL2
SEQ ID NO:8: siRNA for PD-L1 (sh831)
SEQ ID NO:9: siRNA for PD-L1 (sh832)
SEQ ID NO:10: siRNA for PD-L2 (sh833)
SEQ ID NO:11: siRNA for PD-L2 (sh834)
SEQ ID NO:12: real time PCR F-primer for PD-L1
SEQ ID NO:13: real time PCR R-primer for PD-L1
SEQ ID NO:14: real time PCR F-primer for PD-L2
SEQ ID NO:15: real time PCR R-primer for PD-L2
SEQ ID NO:16: real time PCR F-primer for GAPDH
SEQ ID NO:17: real time PCR R-primer for GAPDH
SEQ ID NO:18: siRNA for TCR alpha
SEQ ID NO:19: siRNA for TCR beta

What is claimed is:

1. A method for enhancing the function of a T cell, comprising:
   suppressing ex vivo the expression of Programmed Death-1 Ligand 1 (PD-L1) and/or Programmed Death-1 Ligand 2 (PD-L2) of the T cell, wherein the expression of PD-L1 and/or PD-L2 is suppressed by siRNA for PD-L1 and/or PD-L2 which is directly introduced into the T cell or which is transcribed in the T cell, and
   stimulating ex vivo the T cell,
wherein the function enhancement is the production enhancement of T cell interferon-γ (IFN-γ) and the production amount of IFN-γ in the T cell is increased as compared with a stimulated control T cell which is not suppressed by the siRNA.

2. The method for enhancing the function of a T cell according to claim 1, wherein the T cell is a cytotoxic T cell or a regulatory T cell.

3. The method for enhancing the function of a T cell according to claim 2, wherein the regulatory T cell is a helper T cell, a controlling T cell or a Th17 cell.

4. An isolated T cell with enhanced function, which is suppressed in the expression of PD-L1 and/or PD-L2 and stimulated, wherein the expression of PD-L1 and/or PD-L2 is suppressed by siRNA for PD-L1 and/or PD-L2 which is directly introduced into the T cell or which is transcribed in the T cell, and wherein the function enhancement is the production enhancement of T cell interferon-γ (IFN-γ) and the production amount of IFN-γ in the T cell is increased as compared with a stimulated control T cell which is not suppressed by the siRNA.

5. The isolated T cell with enhanced function according to claim 4, wherein the T cell is a cytotoxic T cell or a regulatory T cell.

6. The isolated T cell with enhanced function according to claim 5, wherein the regulatory T cell is a helper T cell, a controlling T cell or a Th17 cell.

7. A therapeutic agent for a disease showing sensitivity to the T cell with enhanced function according to claim 4, comprising the T cell as an active ingredient.

8. A therapeutic agent for a disease showing sensitivity to the T cell with enhanced function according to claim 5, comprising the T cell as an active ingredient.

9. A therapeutic agent for a disease showing sensitivity to the T cell with enhanced function according to claim 6, comprising the T cell as an active ingredient.

10. The isolated T cell with enhanced function according to claim 4, wherein the siRNA for PD-L1 comprises the nucleotide sequence of SEQ ID NO:1 or SEQ ID NO:9, and wherein the siRNA for PD-L2 comprises the nucleotide sequence of SEQ ID NO:2 or SEQ ID NO:11.

11. A T cell with enhanced function, which is suppressed in the expression of PD-L1 and/or PD-L2, wherein the expression of PD-L1 and/or PD-L2 is suppressed by siRNA for PD-L1 and/or PD-L2, wherein the siRNA for PD-L1 comprises the nucleotide sequence of SEQ ID NO:1 or SEQ ID NO:9, and wherein the siRNA for PD-L2 comprises the nucleotide sequence of SEQ ID NO:2 or SEQ ID NO:11.

* * * * *